US006898978B2

(12) United States Patent
O'Brien et al.

(10) Patent No.: US 6,898,978 B2
(45) Date of Patent: May 31, 2005

(54) GEOMETRY FOR PULSED ACOUSTIC MEASUREMENTS OF PARTICLE SIZE

(75) Inventors: Richard O'Brien, Turramurra (AU); David W. Cannon, Attleboro Falls, MA (US)

(73) Assignee: Colloidal Dynamics Pty Ltd., Eveleigh (AU)

( * ) Notice: Subject to any disclaimer, the term of this patent is extended or adjusted under 35 U.S.C. 154(b) by 0 days.

(21) Appl. No.: 10/469,065

(22) PCT Filed: Feb. 26, 2002

(86) PCT No.: PCT/AU02/00208

§ 371 (c)(1),
(2), (4) Date: Jan. 20, 2004

(87) PCT Pub. No.: WO02/068934

PCT Pub. Date: Sep. 6, 2002

(65) Prior Publication Data

US 2004/0112137 A1 Jun. 17, 2004

(30) Foreign Application Priority Data

Feb. 26, 2001 (AU) .............................................. PR3381

(51) Int. Cl.$^7$ ............................................... G01N 15/00
(52) U.S. Cl. ............................. 73/613; 73/624; 73/644; 73/865.5
(58) Field of Search ......................... 73/613, 614, 618, 73/624, 643, 644

(56) References Cited

U.S. PATENT DOCUMENTS

| 4,907,453 | A | * | 3/1990 | Marlow et al. ................ 73/584 |
| 5,059,909 | A | * | 10/1991 | O'Brien ....................... 324/457 |
| 5,245,290 | A | * | 9/1993 | Cannon et al. ............... 324/457 |
| 5,616,872 | A | * | 4/1997 | O'Brien ...................... 73/865.5 |
| 6,109,098 | A | * | 8/2000 | Dukhin et al. .............. 73/64.42 |
| 6,553,849 | B1 | * | 4/2003 | Scofield et al. ............ 73/865.5 |
| 6,789,427 | B2 | * | 9/2004 | Batzinger et al. ............. 73/614 |

FOREIGN PATENT DOCUMENTS

| GB | 2 350 899 | 12/2000 |
| WO | WO 93/04363 | 3/1993 |
| WO | WO 94/29694 | 12/1994 |

OTHER PUBLICATIONS

Babchin et al., "Electrokinetic Measurements by Electroacoustical Methods", Adcances in Colloidal and Interface Science, vol. 30, No. 1–2, 1989, p. 111–151.

* cited by examiner

Primary Examiner—Hezron Williams
Assistant Examiner—Jacques M. Saint-Surin
(74) Attorney, Agent, or Firm—Kinney & Lange, P.A.

(57) ABSTRACT

An apparatus for making pulsed acoustic measurements to determine particle size in a sample (1) such as a colloid. The apparatus includes two electrodes (2) between which an electric voltage is applied to the sample. The voltage is applied in short pulses. The applied voltage generates an acoustic signal, such as a sound wave (5), in the sample which is detected with a transducer (3) after the wave (5) has passed through a delay element (4). The delay element (4) is used to introduce enough of a time delay between the application of the voltage pulse and sound wave (5) reaching the transducer so that the received wave's signal can be isolated from any signal generated in the transducer (3) by the applied voltage. The delay element (4) and the transducer (3) are arranged into a geometry, or, alternatively, the delay element (4) is shaped, so that any reflections of the sound wave (5) from the sidewalls of the delay element (4) are deflected away from the transducer (3). This reduces interference, particularly at low frequencies.

16 Claims, 3 Drawing Sheets

GEOMETRY FOR PULSED ACOUSTIC MEASUREMENTS OF PARTICLE SIZE

FIELD OF THE INVENTION

The present invention relates to a method and apparatus for use in making pulsed acoustic measurements, particularly ultrasonic measurements.

BACKGROUND OF THE INVENTION

Measurements of the response of a material to a pulsed acoustic signal are used in a variety of applications. Whilst it is more broadly applicable, the present invention will be predominantly described in relation to the field of electroacoustic measurements.

U.S. Pat. Nos. 5,059,909, 5,245,290 and 5,616,872 describe the theory and application of electroacoustic measurements in determining particle size and zeta potential within colloids. They do this by making electroacoustic measurements, which involve the application of a high-frequency (typically MHz) alternating voltage across the colloid. This voltage generates sound waves which are measured by a transducer. From these measurements of sound waves as a function of frequency the particle size and zeta potential of the colloidal particles can be determined. The applicant manufactures commercially a device, marketed as the AcoustoSizer, which measures size and zeta potential using this method.

The AcoustoSizer measurement procedure is illustrated in FIG. 1.

The applied voltage generates sound waves 5. Although these sound waves 5 are generated by the colloid 1, they appear to come from the electrodes 2 (for an explanation see §3 of the paper by O'Brien, Cannon and Rowlands in "Journal of Colloid Interface Science", No. 173, p406–418 (1995)). Thus two sound wave beams are generated; one from each electrode. The signal from the right hand electrode in FIG. 1 is the one used for determining particle size and zeta potential in the AcoustoSizer. When that signal reaches the transducer 3, it generates a small voltage. That voltage is very much smaller than the driving voltage originally applied across the colloid (by a factor of 100,000 or so). This creates a measurement problem, for it is very difficult to completely isolate the leads of the transducer from the large applied voltage, and as a result there will usually be a component of the transducer signal due to "cross talk" from the applied voltage. In order to remove this cross talk the AcoustoSizer uses a combination of pulsed signals and a delay line 4. Instead of applying a continuous sinusoidal voltage across the colloid 1, the AcoustoSizer applies a pulsed sinusoid, which is simply a sinusoid of limited duration—typically a few microseconds. The glass block 4 in the above diagram is the delay line—its function is to introduce a delay between the application of the voltage to the colloid 1 and the sound wave 5 reaching the transducer. When the sound wave 5 has arrived at the transducer 3, the applied voltage has been turned off, and there is no longer any cross talk. The electrode spacing and the pulse width are chosen so that the sound wave pulse from the second electrode reaches the transducer 3 after the sound wave pulse from the closest electrode has finished. Thus the pulses do not overlap in the transducer 3 and it is possible to gate off and measure the signal from the closest electrode.

One limitation of the AcoustoSizer approach to measurement is that it works only if the sound wavelength 5 in the glass block 4 is much smaller than the cross sectional dimensions of the glass block 4. This restricts the device to frequencies above 1 MHz. At lower frequencies the beam spreads out and is reflected from the side walls of the glass block 4. The reflected signals interfere with the signal from the closest electrode and instead of getting two distinct signals from the two electrodes, we obtain one smeared out signal. Thus it is not possible to gate off and measure the signal from the closest electrode.

It is desirable that the delay line be operable at lower frequencies. Larger particles have greater inertia, and so a lower frequency signal will produce larger movements and hence better measurements for colloidal particles which include larger particles. The use of lower frequency measurements in other applications is similarly constrained.

One known low frequency colloid analyser is described in U.S. Pat. No. 4,907,453. A piezoelectric transducer produces a continuous, low frequency, low power acoustic signal. This signal is propagated through a colloid sample towards a receiver. However, the use of an applied voltage to generate an acoustic signal in the colloid is not disclosed and hence the difficulties associated with "cross talk" and the use of a delay line are not considered.

A known device for measuring particle size distribution and zeta potential is described in U.S. Pat. No. 6,109,098. A piezoelectric transducer produces pulsed acoustic signals. These signals are propagated through a colloid sample towards a receiver via quartz delay rods. The device suffers from beam spreading at low frequencies and hence can only be reliably operated above 1 MHz.

A known method of detecting the onset of colloid formation is described in WO 00/74839. An oscillating electric field is applied to a sample and an acoustic signal is generated. This acoustic signal propagates through an acoustic delay line to a detector. This method uses the standard type of delay line. The acoustic signal passes down a rod of fixed cross section and no consideration is given towards focusing the signal beam.

It is an object of the present invention to provide a method for pulsed acoustic measurements, and an apparatus for such measurements, which is operable with wavelengths which are not much smaller than the dimensions of the delay line.

SUMMARY OF THE INVENTION

Broadly, the present invention provides for the use of a delay line, in which the geometry is altered so as to minimise sidewall reflections and their adverse effects on measurement, particularly at the point where the transducer is located. A preferred form uses curved, for example circular, geometry to focus the acoustic waves away from the wall.

According to one aspect, the present invention provides an apparatus for making pulsed acoustic measurements, including means for generating an acoustic response in a sample, a delay element, and a transducer for detecting the acoustic response, characterised in that the delay element and transducer are arranged to have a geometry so as to reduce the effect of sidewall reflections relative to a similarly sized rectangular delay element.

Preferably, the delay element includes interfaces with a curved geometry, so as to deflect the sidewall reflections away from the site of the transducer. In one form, the transducer may be located on the opposite side of a curved element to the source of the acoustic signal. The acoustic signal may be the acoustic response to an electrical pulse across a sample of a colloid.

According to another aspect, the present invention provides an apparatus for making pulsed acoustic measurements, including means for generating an acoustic response in a sample, a delay element, and a transducer for detecting the acoustic response, characterised in that the delay element is shaped so that the walls of the delay element are oriented so that sidewall reflections do not substantially propagate to the transducer.

BRIEF DESCRIPTION OF DRAWINGS

Illustrative embodiments of the present invention will now be described with reference to the accompanying figures, in which.

DETAILED DESCRIPTION OF THE DRAWINGS

The present invention will be described in relation to several possible embodiments of the present invention. It will be appreciated that there are many possible arrangements which can achieve the objects of the invention, and those presented are merely illustrative.

The inventor experimented with a number of geometries for the glass block 4. Other rectangular shapes were tried, as well as cylindrical delay lines—but they all showed substantial sidewall reflections at the transducer 3. The only way to allow for lower operating frequencies with delay lines shaped this way is to increase the cross sectional dimensions of the block. This in turn leads to the dimensions of the instrument being increased, which is undesirable from a cost and space perspective.

Figure 1:
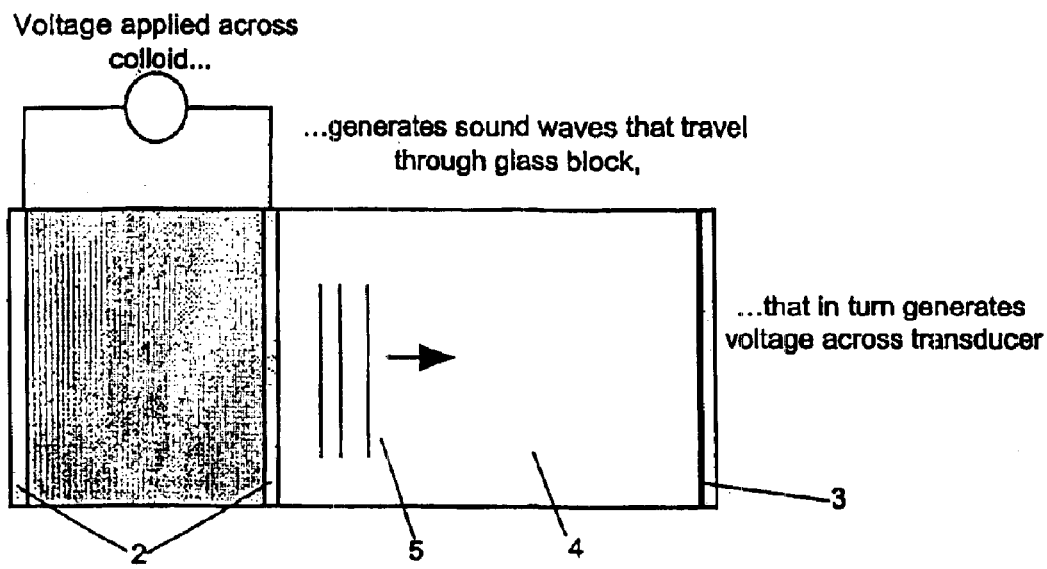
FIG. 1 illustrates schematically the prior art approach to measurement.
Figure 2:
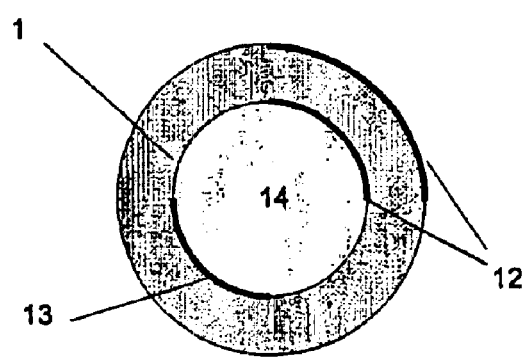
FIG. 2 illustrates a first embodiment of the present invention.

FIG. 2 illustrates a design that uses circular geometry to focus the beams away from the wall. This enables clean electroacoustic pulses to be detected without sidewall reflections smearing the signal.

When the voltage is applied across the electrodes 12, sound waves are generated as in the AcoustoSizer, but because of the circular geometry there is a tendency for the sound waves to be focussed as they move towards the centre of the solid cylinder 14. There will still be some spreading out of the wave, but waves that do hit the sides of the rod will tend to get reflected back, rather than being directed to the transducer 13. As a result the signals from the first electrode is not overlapped by any other signals, and we can make our measurement, even though the wavelength is not small compared to the rod diameter.

Figure 5:
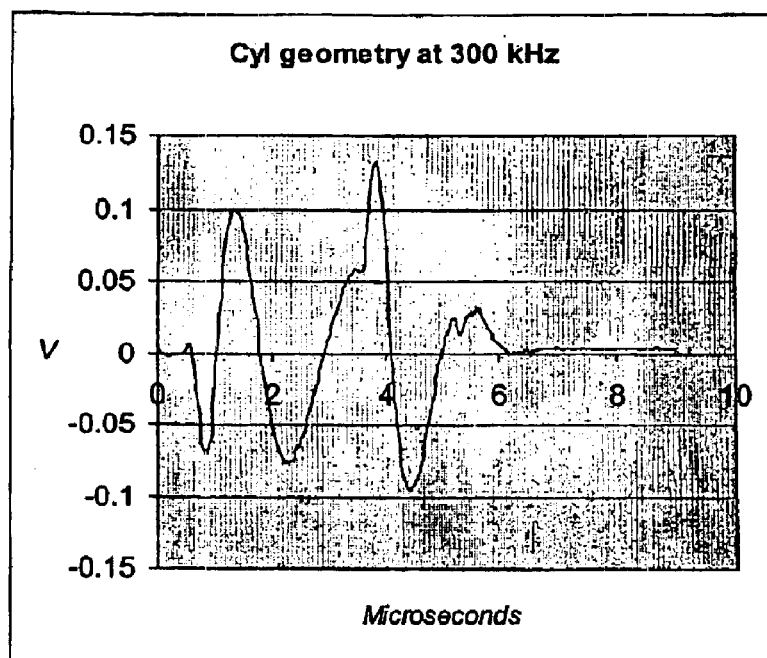
FIG. 5 illustrates a typical transducer signal using an embodiment of the present invention.
Figure 6:
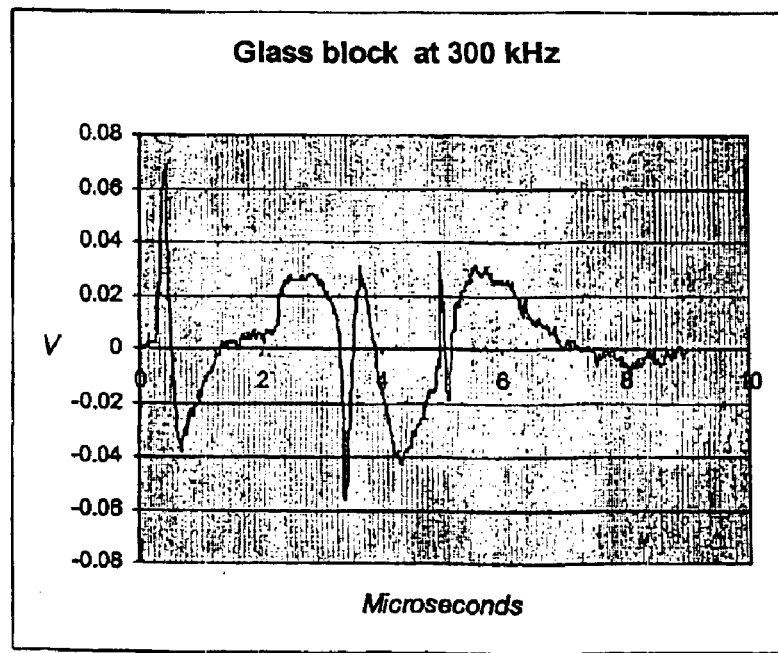
FIG. 6 illustrates a typical transducer signal using the background art device.

FIGS. 5 and 6 illustrate the advantage of the cylindrical geometry. FIG. 5 illustrates the transducer signal at 300 kHz using the device geometry shown in FIG. 2. In this case the diameter d of the solid cylinder 4, which is made of plastic, is 30 mm. The sound wavelength $\lambda$ in the plastic is 7.3 mm at this frequency, and thus the ratio d/$\lambda$ is approximately 4. FIG. 6 shows the waveform obtained using a rectangular glass block at the same frequency. The cross sectional dimensions of the block have been chosen to give the same d$\lambda$ ratio. In this example, the block has a square cross sectional area having sides of approximately 70 mm. Clearly the gated waveform in FIG. 6 is much more smeared out; and it cannot be readily used for measurement as it cannot be easily gated.

Figure 3:
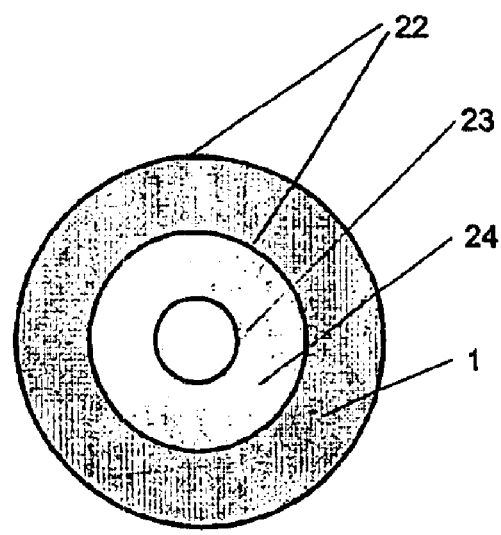
FIG. 3 illustrates a second embodiment of the present invention.

FIG. 2 shows only one possible implementation. FIG. 3 illustrates another possible geometry including an annular device with a concentric cylinder geometry. The electrodes 22 are cylindrical and contain sample 1. This has the advantage that the beam from the colloid 1 is focused onto the central transducer 23, and in the focussing it will be amplified. The disadvantage compared to the design in FIG. 2 is that it has to be larger in order to have same delay between the applied pulse and the sound wave arriving at the transducer 23.

Figure 4:
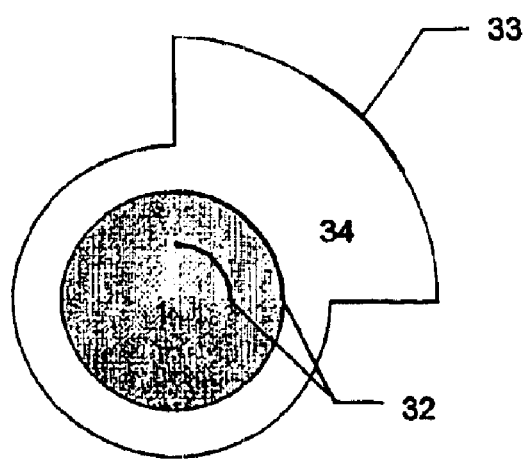
FIG. 4 illustrates a third embodiment of the present invention.

FIG. 4 illustrates a further implementation of the present invention. In this device the colloid 1 is contained in a central cup and the transducer 33 is on the outer part of the design. Electrodes 32 are arranged to point towards transducer 33. So, the beam from the colloid 1 is spread out, rather than being focussed. The sidewall reflections are reduced because of the divergence of the sidewalls in delay element 34. The advantage of this device is that it would be easier to stir the colloid 1 in this cup than in the annular geometries above.

The examples provided have centered on the problem of measuring the electroacoustic signal using the pulse-delay line technique. There are other measurements that are also made by pulse-delay line techniques. These include ultrasonic attenuation, speed of sound and acoustic impedance of a material. In these measurements the voltage is applied across a transducer rather than the colloid. A sound wave is generated and that sound wave is then measured after passing through or being reflected by the material. Although the measurement is different the principle is the same: by using an altered geometry, it is possible to use lower frequencies for a given size of apparatus.

It will be appreciated that additions and variations are possible within the scope of the present invention, without departing from the general inventive concept.

What is claimed is:

1. An apparatus for making pulsed acoustic measurements, including means for generating an acoustic response in a sample, a delay element, and a transducer for detecting the acoustic response, the transducer being positioned so as to receive said response through said delay element, characterised in that the delay element and transducer are arranged to have a geometry so as to reduce the effect of sidewall reflections relative to a similarly sized rectangular block delay element.

2. An apparatus according to claim 1, wherein the delay element includes interfaces with a curved geometry, so as to deflect the sidewall reflections away from the site of the transducer.

3. An apparatus according to claim 2, wherein the transducer is located on the opposite side of a curved element to a source of an acoustic signal.

4. An apparatus according to claim 3, wherein the acoustic signal is the acoustic response to an electric pulse across a sample of a colloid.

5. An apparatus for making pulsed acoustic measurements, including means for generating an acoustic response in a sample, a delay element, and a transducer for detecting the acoustic response, the transducer being positioned so as to receive said response through said delay element, characterised in that the delay element is shaped so that the walls of the delay element are orientated so that sidewall reflections do not substantially propagate to the transducer.

6. An apparatus according to claim 5, wherein the delay element includes interfaces with a curved geometry, so as to deflect the sidewall reflections away from the site of the transducer.

7. An apparatus according to claim 6, wherein the transducer is located on the opposite side of a curved element to a source of an acoustic signal.

8. An apparatus according to claim 7, wherein the acoustic signal is the acoustic response to an electric pulse across a sample of a colloid.

9. A method for making pulsed acoustic measurements, including the steps of:

generating an acoustic response in a sample;

providing a delay element through which an acoustic signal arising from the acoustic response propagates; and providing a transducer which detects the acoustic signal propagated from the delay element;

characterised by arranging the delay element and transducer into a geometry which reduces the effect of sidewall reflections when compared to a similarly sized rectangular block delay element.

10. A method according to claim 9, wherein the delay element includes interfaces with a curved geometry, so as to deflect the sidewall reflections away from the site of the transducer.

11. A method according to claim 10, wherein the transducer is provided on the opposite side of a curved element to the source of the acoustic signal.

12. A method according to claim 11, wherein the acoustic signal is the acoustic response to an electric pulse across a sample of a colloid.

13. A method for making pulsed acoustic measurements, including the steps of:

generating an acoustic response in a sample;

providing a delay element through which an acoustic signal arising from the acoustic response propagates; and providing a transducer which detects the acoustic signal propagated from the delay element;

characterised by providing a delay element having a shape, wherein the walls of the delay element are orientated so that sidewall reflections do not substantially propagate to the transducer.

14. A method according to claim 13, wherein the delay element includes interfaces with a curved geometry, so as to deflect the sidewall reflections away from the site of the transducer.

15. A method according to claim 14, wherein the transducer is provided on the opposite side of a curved element to the source of the acoustic signal.

16. A method according to claim 15, wherein the acoustic signal is the acoustic response to an electric pulse across a sample of a colloid.

* * * * *